(12) United States Patent
Bhatia et al.

(10) Patent No.: US 11,837,353 B2
(45) Date of Patent: Dec. 5, 2023

(54) SYSTEMS AND METHODS FOR PREDICTING IMAGE QUALITY SCORES OF IMAGES

(71) Applicant: HeartFlow, Inc., Redwood City, CA (US)

(72) Inventors: Vivek Naresh Bhatia, Santa Clara, CA (US); Leo J. Grady, Darien, CT (US); Souma Sengupta, Cupertino, CA (US); Timothy A. Fonte, San Francisco, CA (US)

(73) Assignee: HeartFlow, Inc., Mountain View, CA (US)

( * ) Notice: Subject to any disclaimer, the term of this patent is extended or adjusted under 35 U.S.C. 154(b) by 0 days.

(21) Appl. No.: 17/575,926

(22) Filed: Jan. 14, 2022

(65) Prior Publication Data

US 2022/0139529 A1 May 5, 2022

Related U.S. Application Data

(63) Continuation of application No. 16/742,133, filed on Jan. 14, 2020, now Pat. No. 11,257,585, which is a
(Continued)

(51) Int. Cl.
*G06T 7/00* (2017.01)
*A61B 6/00* (2006.01)
(Continued)

(52) U.S. Cl.
CPC ............ *G16H 30/20* (2018.01); *A61B 6/032* (2013.01); *A61B 6/488* (2013.01); *A61B 6/503* (2013.01);
(Continued)

(58) Field of Classification Search
CPC ........ G16H 30/20; G16H 30/40; G16H 40/63; G16H 50/20; G16H 50/70; G16H 30/00;
(Continued)

(56) References Cited

U.S. PATENT DOCUMENTS

| 4,835,690 A | 5/1989 | Gangarosa et al. |
| 8,315,812 B2 | 11/2012 | Taylor |

(Continued)

FOREIGN PATENT DOCUMENTS

| CN | 101686825 A | 3/2010 |
| WO | WO 2004/057515 A2 | 7/2004 |
| WO | WO 2013/075127 A1 | 5/2013 |

OTHER PUBLICATIONS

Afina Glas, Jeroen G. Lijmer, Martin H. Prins, Gouke J. Bonsel, and Patrick M.M. Bossuyt: "The Doiagnotic Odds Ratio: A Single Indicator of Test Perfrmance"; Apr. 17, 2003; Journal of Clinical Epidemiology 56 (2003) pp. 1129-1135. (Year: 2003).*
(Continued)

*Primary Examiner* — Siamak Harandi
(74) *Attorney, Agent, or Firm* — Bookoff McAndrews, PLLC (57) ABSTRACT

Systems and methods are disclosed for identifying image acquisition parameters. One method includes receiving a patient data set including one or more reconstructions, one or more preliminary scans or patient information, and one or more acquisition parameters; computing one or more patient characteristics based on one or both of one or more preliminary scans and the patient information; computing one or more image characteristics associated with the one or more reconstructions; grouping the patient data set with one or more other patient data sets using the one or more patient characteristics; and identifying one or more image acquisition parameters suitable for the patient data set using the one
(Continued)

or more image characteristics, the grouping of the patient data set with one or more other patient data sets, or a combination thereof.

16 Claims, 4 Drawing Sheets

Related U.S. Application Data continuation of application No. 15/680,728, filed on Aug. 18, 2017, now Pat. No. 10,572,998, which is a continuation of application No. 15/088,732, filed on Apr. 1, 2016, now Pat. No. 9,805,470, which is a continuation of application No. 14/734,060, filed on Jun. 9, 2015, now Pat. No. 9,330,233, which is a continuation of application No. 14/506,293, filed on Oct. 3, 2014, now Pat. No. 9,152,761.

(60) Provisional application No. 61/925,947, filed on Jan. 10, 2014.

(51) Int. Cl.
*G16H 30/20* (2018.01)
*G16H 40/63* (2018.01)
*G16H 50/20* (2018.01)
*G16H 30/40* (2018.01)
*G06F 18/24* (2023.01)
*G06T 5/00* (2006.01)
*A61B 6/03* (2006.01)
*G16H 50/70* (2018.01)

(52) U.S. Cl.
CPC ............... *G06F 18/24* (2023.01); *G06T 5/00* (2013.01); *G06T 7/00* (2013.01); *G06T 7/0012* (2013.01); *G16H 30/40* (2018.01); *G16H 40/63* (2018.01); *G16H 50/20* (2018.01); *G06T 2207/10081* (2013.01); *G06T 2207/30048* (2013.01); *G16H 50/70* (2018.01); *Y02A 90/10* (2018.01)

(58) Field of Classification Search
CPC ......... A61B 6/032; A61B 6/488; A61B 6/503; G06F 18/24; G06T 5/00; G06T 7/00; G06T 7/0012; G06T 2207/10081; G06T 2207/30048; Y02A 90/10; G06V 10/40; G06V 10/467
See application file for complete search history.

(56) References Cited

U.S. PATENT DOCUMENTS

| | | |
|---|---|---|
| 2005/0010445 A1 | 1/2005 | Krishnan et al. |
| 2010/0086189 A1 | 4/2010 | Wang et al. |
| 2010/0183206 A1* | 7/2010 | Carlsen ................. A61B 6/488 382/128 |
| 2011/0110572 A1 | 5/2011 | Guehring et al. |
| 2012/0014499 A1 | 1/2012 | Feuerlein |
| 2012/0041779 A1 | 2/2012 | Boroczky et al. |
| 2012/0190962 A1 | 7/2012 | Glaser-Seidnitzer et al. |
| 2012/0213326 A1 | 8/2012 | Walker et al. |
| 2012/0299916 A1 | 11/2012 | Giphart et al. |
| 2013/0105699 A1 | 5/2013 | Asma |
| 2013/0136328 A1 | 5/2013 | Jansen |
| 2013/0261462 A1 | 10/2013 | Wantanabe |
| 2013/0311427 A1 | 11/2013 | Patel et al. |
| 2013/0311472 A1 | 11/2013 | Cohen-Solal et al. |
| 2016/0140300 A1 | 5/2016 | Purdie et al. |

OTHER PUBLICATIONS

Kirbas, Cemil et al., A review of Vessel Extraction Techniques and Algorithms, Jun. 2004, pp. 81-121, vol. 36, No. 2, ACM Computing Surveys.

Search Report and Written Opinion dated May 4, 2015, in corresponding International Application No. PCT/US2015/010578, filed on Jan. 8, 2015 (10 pages).

Feedback from Wikipedia, the free encyclopedia, Jan. 3, 2017, (11 pages).

Anonymous: "Feedback", Wikipedia, Jan. 9, 2014 (Jan. 9, 2014), Retrieved from the Internet: URL:https://en.wikipedia.org/w/index.php?title=Feedback&oldid=589913357.

Dave Fornell: "Iterative Reconstruction 101", Imaging Technology News, Jul. 23, 2013 (Jul. 23, 2013) (4 pages).

"Machine Learning" as published on Dec. 17, 2013, Wikipedia, retrieved from the Internet: https://en.wikipedia.org/w/index.php?title=Machine_learning&oldid=586518404, accessed May 6, 2021 (9 pages).

* cited by examiner

SYSTEMS AND METHODS FOR PREDICTING IMAGE QUALITY SCORES OF IMAGES

RELATED APPLICATION(S)

This application is a continuation of and claims the benefit of priority to U.S. application Ser. No. 16/742,133, filed on Jan. 14, 2020, which is a continuation of and claims the benefit of priority to U.S. application Ser. No. 15/680,728, filed Aug. 18, 2017, now U.S. Pat. No. 10,572,998, which is a continuation of and claims the benefit of priority to U.S. application Ser. No. 15/088,732, filed Apr. 1, 2016, now U.S. Pat. No. 9,805,470, which is a continuation of and claims the benefit of priority to U.S. application Ser. No. 14/734,060, filed Jun. 9, 2015, now U.S. Pat. No. 9,330,233, which is a continuation of and claims the benefit of priority to U.S. application Ser. No. 14/506,293, filed Oct. 3, 2014, now U.S. Pat. No. 9,152,761, which claims priority to U.S. Provisional Application No. 61/925,947, filed Jan. 10, 2014, all of which are hereby incorporated by reference in their entireties.

FIELD OF THE INVENTION

Various embodiments of the present disclosure relate generally to imaging and related methods. More specifically, particular embodiments of the present disclosure relate to systems and methods for identifying medical image acquisition parameters.

BACKGROUND

Imaging may be critical in many commercial settings. Users of imaging may include any range of professionals or consumers. As one example, medical doctors, technicians, and/or other individuals trained to acquire medical images may all employ imaging to make patient care decisions. Medical imaging may include radiography, computed tomography (CT), magnetic resonance imaging (MRI), fluoroscopy, single-photon emission computed tomography (SPECT), positron emission tomography (PET), scintigraphy, ultrasound, as well as specific techniques (e.g., echocardiography, mammography, intravascular ultrasound, and angiography).

By way of example, one application of medical imaging is the diagnosis and treatment of coronary artery disease, which may produce coronary lesions in the blood vessels providing blood to the heart, such as a stenosis (abnormal narrowing of a blood vessel). Patients suffering from coronary artery disease may experience a restriction of blood flow to the heart and resulting chest pain, referred to as chronic stable angina during physical exertion or unstable angina when the patient is at rest. A more severe manifestation of disease may lead to myocardial infarction, or heart attack.

Patients suffering from chest pain and/or exhibiting symptoms of coronary artery disease may be subjected to one or more noninvasive tests that may provide some indirect evidence relating to coronary lesions. For example, noninvasive tests may include electrocardiograms, biomarker evaluation from blood tests, treadmill tests, echocardiography, SPECT, and PET. Anatomic data may be obtained noninvasively using coronary computed tomographic angiography (cCTA). cCTA may be used for imaging of patients with chest pain. For example, cCTA may involve using CT technology to image the heart and the coronary arteries following an intravenous infusion of a contrast agent.

Although use of imaging may be pervasive, the image acquisition process still has limitations. For example, in the medical context, trade-offs may lie between capturing an image of a quality high enough to provide information to make a medical decision (e.g., a diagnosis), while at the same time, minimizing risk to a patient (e.g., from radiation exposure) and resources used for the image acquisition. Therefore, a desire may exist to identify or anticipate image acquisition parameters that may produce images of requisite quality, while limiting traditional drawbacks, e.g., radiation exposure and resource usage associated with quality imaging. In other words, a desire may exist for determining or obtaining optimized image acquisition parameters, for instance, prior to obtaining an image or scan.

The foregoing general description and the following detailed description are exemplary and explanatory only and are not restrictive of the disclosure.

SUMMARY

According to certain aspects of the present disclosure, systems and methods are disclosed for identifying image acquisition parameters. One method includes: receiving a patient data set including one or more reconstructions, one or more preliminary scans or patient information, and one or more acquisition parameters; computing one or more patient characteristics based on one or both of one or more preliminary scans and the patient information; computing one or more image characteristics associated with the one or more reconstructions; grouping the patient data set with one or more other patient data sets using the one or more patient characteristics; and identifying one or more image acquisition parameters suitable for the patient data set using the one or more image characteristics, the grouping of the patient data set with one or more other patient data sets, or a combination thereof.

In accordance with another embodiment, a system for identifying image acquisition parameters comprises: a data storage device storing instructions for identifying image acquisition parameters; and a processor configured for: receiving a patient data set including one or more reconstructions, one or more preliminary scans or patient information, and one or more acquisition parameters; computing one or more patient characteristics based on one or both of one or more preliminary scans and the patient information; computing one or more image characteristics associated with the one or more reconstructions; grouping the patient data set with one or more other patient data sets using the one or more patient characteristics; and identifying one or more image acquisition parameters suitable for the patient data set using the one or more image characteristics, the grouping of the patient data set with one or more other patient data sets, or a combination thereof.

In accordance with yet another embodiment, a non-transitory computer readable medium for use on a computer system containing computer-executable programming instructions for identifying image acquisition parameters is provided. The method includes: receiving a patient data set including one or more reconstructions, one or more preliminary scans or patient information, and one or more acquisition parameters; computing one or more patient characteristics based on one or both of one or more preliminary scans and the patient information; computing one or more image characteristics associated with the one or more reconstructions; grouping the patient data set with one or more other patient data sets using the one or more patient characteristics; and identifying one or more image acquisition parameters suitable for the patient data set using the one or more image characteristics, the grouping of the patient data set with one or more other patient data sets, or a combination thereof.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

Imaging may be critical in many commercial settings. In particular, medical imaging may be ubiquitous in providing healthcare. Still, there may exist several limitations, both to information that imaging may provide, as well as limitations in image acquisition. Regarding information limitations, medical imaging information from non-invasive diagnostic imaging for coronary artery disease may come with well-known limitations in defining the anatomy of lesions in the coronary arteries. For instance, methods are still being refined for obtaining accurate data relating to coronary lesions, e.g., size, shape, location, functional significance (e.g., whether the lesion impacts blood flow), etc. based on imaging. Regarding image acquisition limitations, medical imaging may involve weighing a priority of obtaining a high quality image, against for instance, resources expended and/or patient radiation exposure.

Image acquisition parameters (e.g., x-ray tube voltage, x-ray beam filter, detector configuration, exposure time, frames per unit time, frames per trigger, device-specific settings, slice thickness, scan mode, rotation time, etc.) may be initialized prior to acquiring an image. The quality of images may vary based on an imaging subject (e.g., a patient with high BMI may require parameters distinct from parameters of a patient with low BMI, or patients with different cardiac output may require different scan times, etc.), a particular image acquisition instrument (e.g., physical dimensions of optical components, output x-ray characteristics, a helical CT scanner in a particular room of a specific hospital, etc.), operator characteristics (e.g., various processes or idiosyncrasies associated with people or entities operating instruments for image acquisition, etc.), and/or preliminary images (e.g., scout images) that may be used to prescribe, check, and/or calibrate the image acquisition. The parameters may impact the quality of an acquired image, meaning an optimal set of acquisition parameters may contribute to producing a high quality image. However, acquisition parameters are generally population-based or parameters dictated by general or standard imaging protocols. Acquisition parameters are not tailored for a particular patient's specific anatomy or specific anatomy being imaged and the particular task at hand. For example, imaging dose for imaging small features with low contrast density variation (e.g., plague) may differ from suitable imaging dose for imaging large features with high contrast density variation (e.g., myocardial perfusion). Image acquisition may not take into account such distinctions that may improve resultant imaging. Thus, a desire exists to identify image acquisition parameters that may produce a high quality image.

The present disclosure is directed to systems and methods for identifying medical image acquisition parameters, and, more particularly, to systems and methods for iteratively optimizing image acquisition and reconstruction parameters to produce high quality medical images, including images involved in cardiac CT image acquisition. As described above, the quality of medical images may be influenced by one or more of: population-based or standard image acquisition parameters, the imaging subject, the particular image acquisition instrument, and preliminary images. The present disclosure is directed to using historical data and/or machine learning techniques to train one or more computing systems to predict an optimal set of image acquisition parameters that may produce a high quality image while limiting unfavorable imaging conditions. In addition to an exemplary general embodiment, the present disclosure describes embodiments relating to predicting image acquisition parameters based on preliminary scans, including scout, calcium scoring scans, operator characteristics, and/or contrast timing scans. As an extension, predicting image acquisition parameters may also entail predicting an image quality based on image quality produced by past images acquired using the same image acquisition parameters.

In one embodiment, the disclosed techniques for identifying and optimizing medical image acquisition parameters may be applicable to and used in connection with methods for estimating patient-specific blood flow characteristics, such as those methods described in U.S. Pat. No. 8,315,812 issued Nov. 20, 2012, to Charles A. Taylor, the entire disclosure of which is incorporated by reference herein. Although certain embodiments of the present disclosure are described, for purposes of example, with respect to the diagnosis and treatment of coronary artery disease, the systems and methods described herein are applicable to the prediction of optimal sets of image acquisition parameters in relation to any field of medical imaging.

Specifically, the present disclosure may be directed to a training phase, where a system may learn and/or create a model that may distill relationships between three sets of information: patient characteristics, acquisition parameters, operator characteristics and/or image quality. The training phase may include processing data associated with a plurality of individuals to develop an understanding of how various patient characteristics and acquisition parameters may impact image quality. By extension, the present disclosure may be further directed to a production phase of determining acquisition parameters that may help produce images of a particular quality, with respect to a particular patient for the target imaging application. For example, the production phase may include finding acquisition parameters that may yield an optimal image quality for the desired imaging application, in light of characteristics specific to the particular patient, acquisition instrument, and/or desired target acquisition parameter. In some cases, a target acquisition parameter may define a priority either in image quality and/or acquisition (e.g., where a priority may include minimizing radiation exposure). In addition to outputting optimized acquisition parameters, the production phase may further include producing high quality images based on the optimized acquisition parameters. In some cases, the systems and methods described may be pertinent to acquisition of cardiac CT images.

Figure 1:
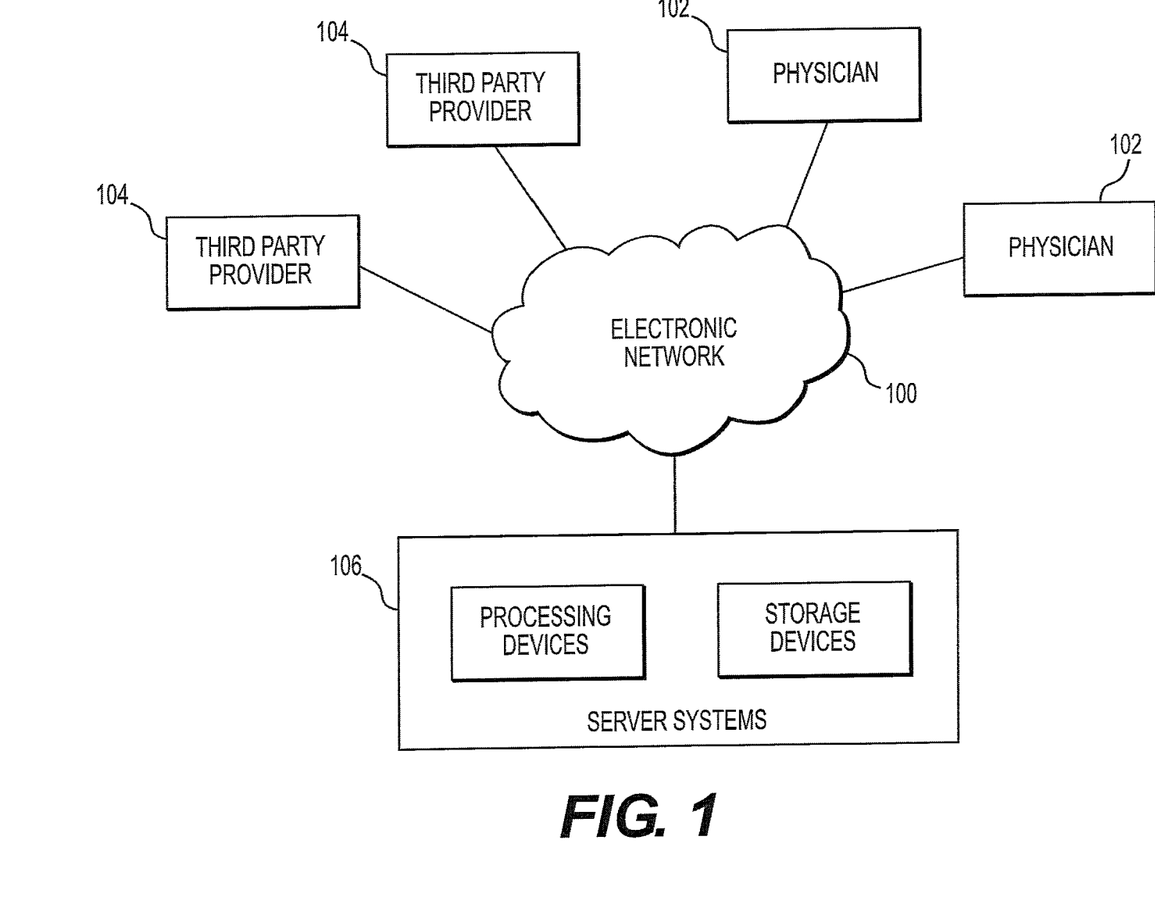
FIG. 1 is a block diagram of an exemplary system and network for identifying image acquisition parameters, according to an exemplary embodiment of the present disclosure.

Referring now to the figures, FIG. 1 depicts a block diagram of an exemplary system and network for identifying image acquisition parameters, according to an exemplary embodiment. Specifically, FIG. 1 depicts a plurality of physicians 102 and third party providers 104, any of whom may be connected to an electronic network 100, such as the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific information, such as age, medical history, blood pressure, blood viscosity, etc. Physicians 102 and/or third party providers 104 may transmit the anatomical images and/or patient-specific information to server systems 106 over the electronic network 100. Server systems 106 may include storage devices for storing images and data received from physicians 102 and/or third party providers 104. Server systems 106 may also include processing devices for processing images and data stored in the storage devices.

Figure 2:
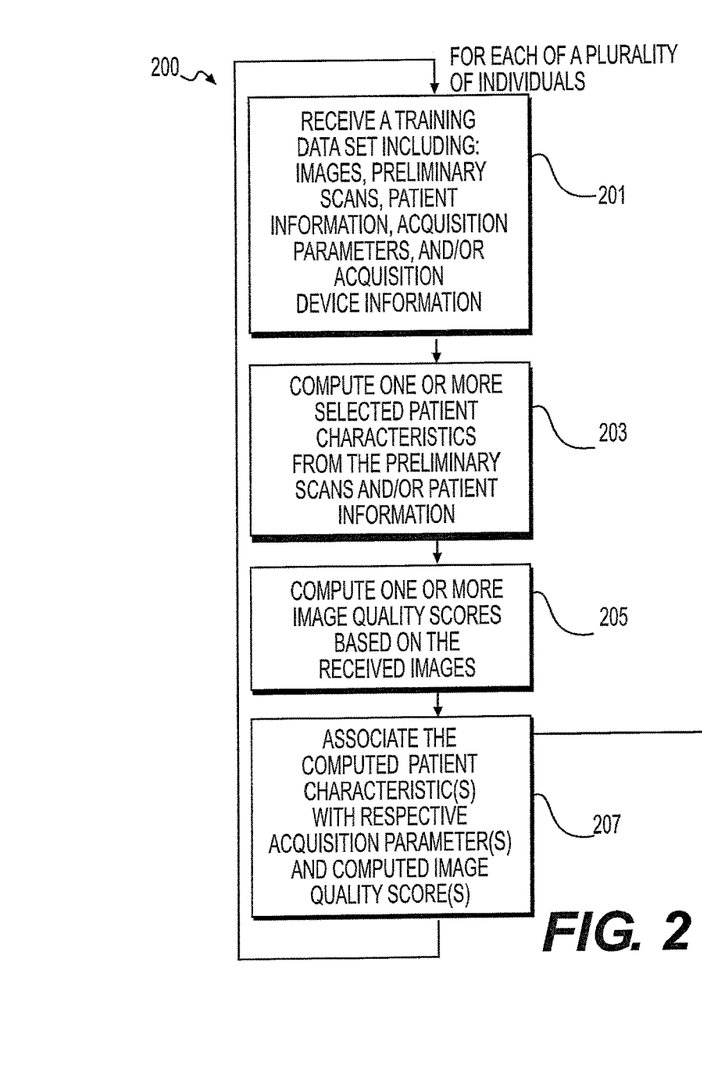
FIG. 2 is a block diagram of an exemplary method of a training phase for developing a model that can be used to predict image quality of primary imaging data, according to an exemplary embodiment of the present disclosure.
Figure 3:
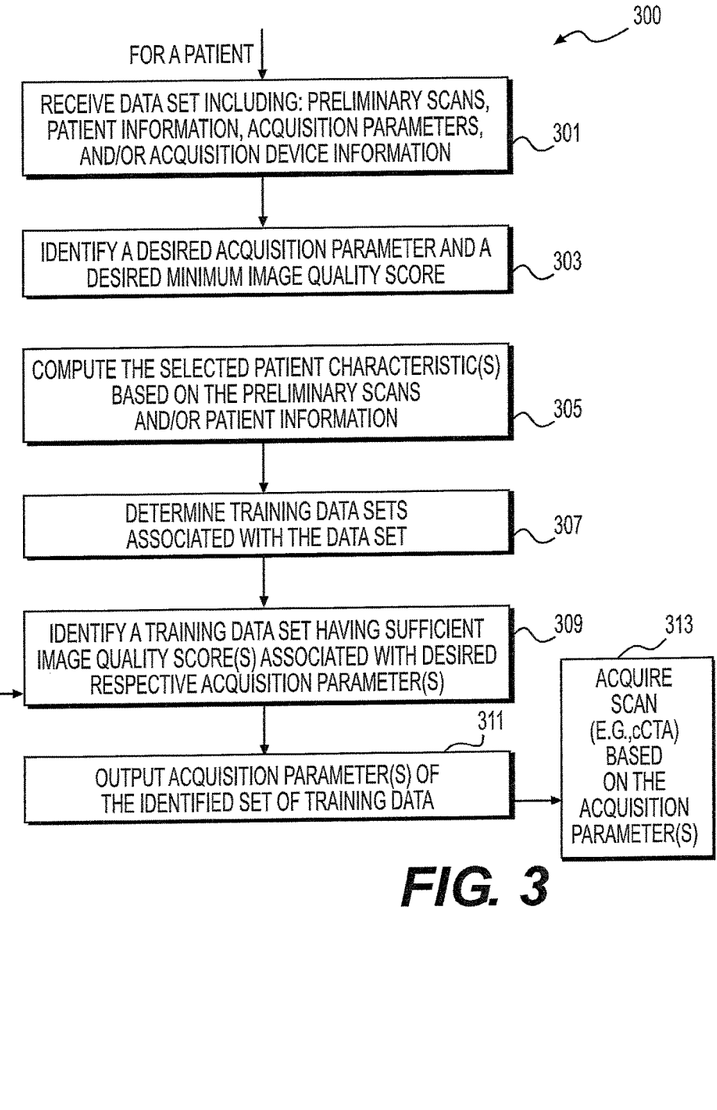
FIG. 3 is a block diagram of an exemplary method of a production phase for finding image acquisition parameters to achieve a desired image quality, based on the training phase model and circumstances associated with primary imaging data, according to an exemplary embodiment of the present disclosure.
Figure 4:
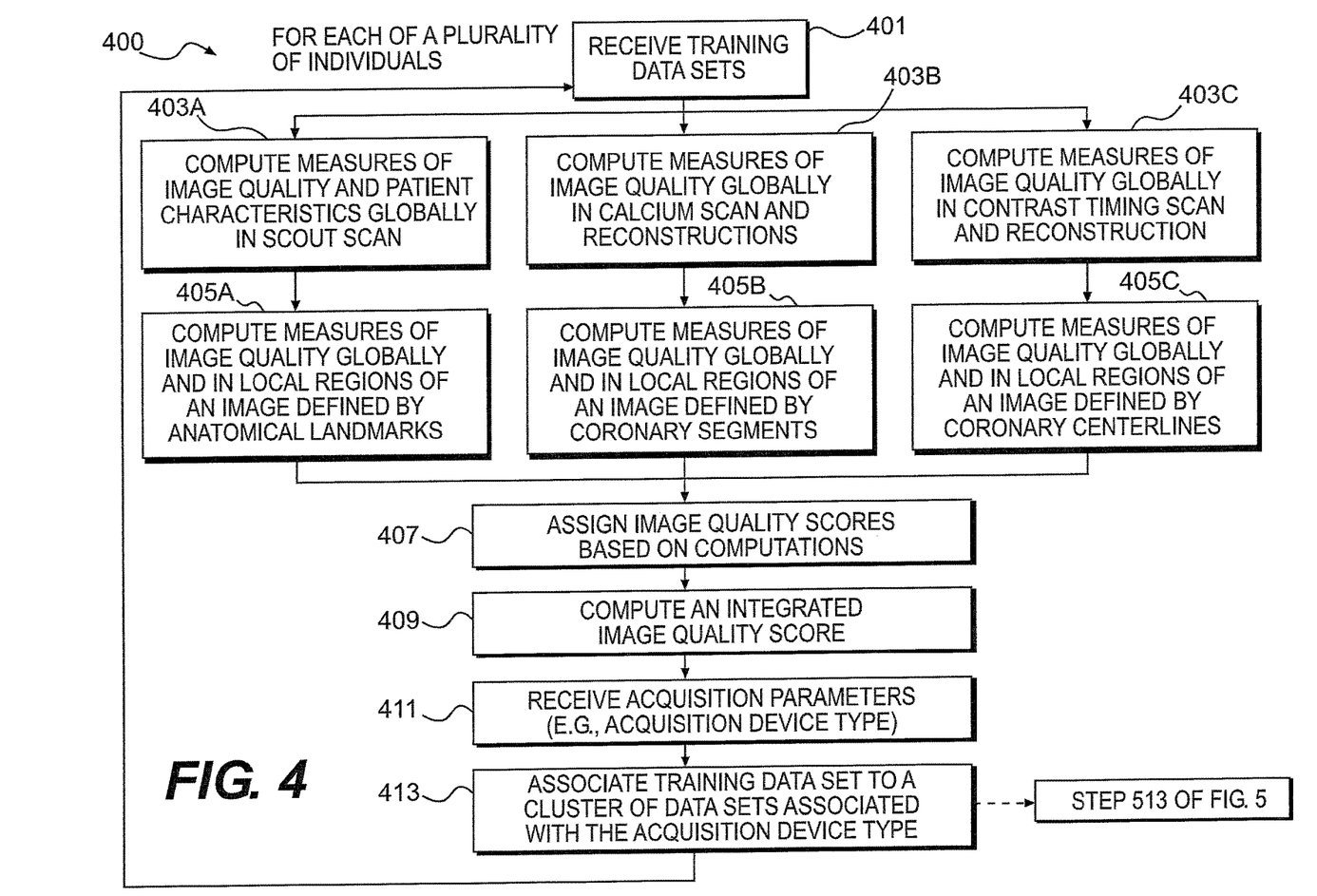
FIG. 4 is a block diagram of an exemplary method of a specific training phase for developing a model using various types of preliminary scans or images, according to an exemplary embodiment of the present disclosure.
Figure 5:
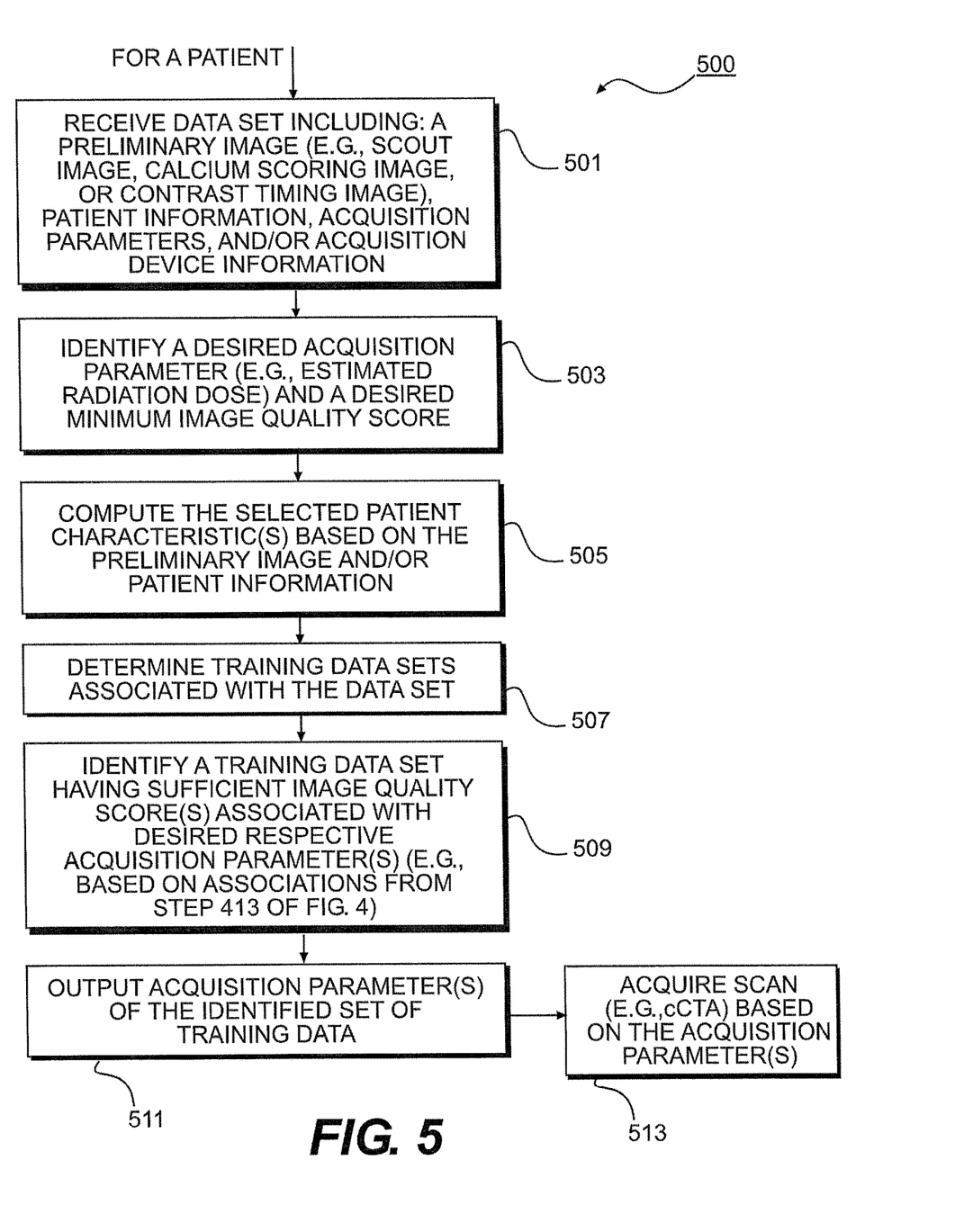
FIG. 5 is a block diagram of an exemplary method of a specific production phase for predicting image quality of medical images, according to an exemplary embodiment of the present disclosure.

FIG. 2 is directed to a general embodiment for a method of training a model to learn associations between an imaging subject (e.g., a patient), acquisition parameters (including parameters used for imaging and/or an image acquisition instrument/device), operator characteristics, and preliminary scans (e.g., images of the imaging subject acquired using the acquisition parameters). FIG. 3 is directed to a general embodiment for a method of producing an output of image acquisition parameters suitable for a particular patient, based on the model of associations from the method in FIG. 2. In some embodiments, the parameters output of FIG. 3 may be taken as recommendations for image acquisition parameters. More specifically, the parameters output from the method and FIG. 3 may include parameters for producing quality images under designated conditions including imaging subjects and image acquisition instruments or devices. In other words, the method of FIG. 3 may provide image acquisition parameters to optimize image quality for capturing a specified image subject using a specified image acquisition device, based on image quality of images of the same (or similar) imaging subject(s), using the same (or similar) image acquisition instrument(s)/device(s), and for the same operator. FIG. 4 is directed to a specific embodiment of a training phase of developing models, wherein the embodiments describe training models based on various types of preliminary scans or images. The exemplary preliminary scans may include scout scans, calcium scans, contrast timing scans, previous scans of a single or selected modality (e.g., a modality that is the same as an imaging modality to be used for imaging anatomy of the particular patient), and/or previous scans of different modalities. FIG. 5 is directed to a specific embodiment of a production phase of using the models to determine image acquisition parameters for producing a quality medical image, for a given imaging subject and image acquisition device.

FIG. 2 is a block diagram of an exemplary method 200 of a training phase for developing a model that can be used to predict image quality of primary imaging data, based on preliminary scans, operator characteristics, acquisition parameters, and reconstructions, according to an exemplary embodiment. The method of FIG. 2 may be performed by server systems 106, based on information, images, and data received from physicians 102 and/or third party providers 104 over electronic network 100. In some embodiments, the predicted image quality may include image quality of primary imaging data, e.g., predicting the quality of a cCTA scan, prior to acquiring the scan.

The training phase essentially builds an understanding of associations between patient characteristics, acquisition parameters, and image quality. Method 200 may train a system to associate patient characteristics (from preliminary scans and/or patient information) with acquisition parameters and image quality. Specifically, in one embodiment, method 200 may include a system (e.g., including server systems 106), receiving multiple electronic representations of data sets comprised of: one or more reconstructions of medical images, one or more preliminary scans (e.g., scout images) and/or patient information, acquisition parameters, operator characteristics, acquisition device information, etc. For example, the electronic representations may be transmitted via a hard drive, cloud architecture, etc. For each data set, the system may compute image and patient characteristics from the received preliminary scan images and/or patient information. The system may further compute, for each data set, several image characteristics of the received reconstructions. For example, image characteristics may include measures of global image quality and image quality in local regions of the received reconstructions. For each acquisition device type then, the system may assign one or more clusters. The assignments may be based on the patient characteristics computed from the preliminary scans in each data set. In some embodiments, the clusters may refer to groupings of data, e.g., bundles or networks of the data sets based on similarities in patient characteristics associated with each data set, as well as data set associations with the acquisition device type. The block diagram of FIG. 2 shows method 200 with a focus on how the system may process each data set to develop a model providing insight into resultant image characteristics from various acquisition and patient variables.

In one embodiment, step 201 may include receiving a training data set for each of a plurality of individuals. As previously discussed, the set may include reconstructions of medical images, patient scout images and information, and acquisition parameters. Next, step 203 may include computing and/or finding image and patient characteristics for each data set. For instance, step 203 may include determining metadata tags for each set, where the tags may characterize image and patient characteristics derived from the received patient scout images and information. Next, step 205 may include computing image characteristics of processed images in the received set. For example, step 205 may include computing image quality characteristics of the reconstructions in the received set. Once image and patient characteristics for the set have been determined, step 207 may be initiated. Step 207 may include associating the set with acquisition parameters. For example, step 207 may include determining several acquisition device types and providing identification or retrieval information for the set based on a respective acquisition device (or acquisition device type) used to produce the set. Furthermore, step 207 may include placing the set in a grouping based on its associated acquisition parameters. For example, step 207 may include placing the set into a cluster based on the computed patient characteristics (e.g., from step 203). Several clusters may be arranged in terms of their associations to acquisition parameters (e.g., including an acquisition device type). The model resulting from method 200 may include sets of data, defined by patient characteristics, image characteristics, operator characteristics, and acquisition data. Once parameters for acquisition are defined (e.g., specifying an acquisition device type), the model may output patient characteristics and optionally, an expected or predicted resultant image quality. Alternately, the model may also output acquisition parameters and corresponding image quality for the target imaging application, if given information regarding patient characteristics. Such outputs are based on the training data sets and associations between patient characteristics, image characteristics, operator characteristics, and acquisition data achieved by exemplary training method 200. FIG. 3 includes further detail regarding the outputs, or use, of method 200.

FIG. 3 is a block diagram of an exemplary method 300 of a production phase for finding image acquisition parameters to achieve a desired image quality, given specific patient characteristics, according to an exemplary embodiment. The method of FIG. 3 may be performed by server systems 106, based on information, images, and data received from physicians 102 and/or third party providers 104 over electronic network 100. Method 300 may be executed on a system (e.g., server systems 106), where the system for method 300 may be the same system, or a different system that may perform method 200. In some embodiments, method 300 may be automated, where a system running method 300 may include an automated image acquisition parameter system.

In some embodiments, once the system has learned to associate patient and operator characteristics with acquisition parameters and image quality (e.g., from method 200), method 300 may be used to predict optimal image scan parameters to produce images of acceptable image quality, in light of provided patient characteristics. In one embodiment, step 301 may include receiving a data set. In some instances, this data set may pertain to a particular patient and be used as a data set for production (e.g., image acquisition production or image acquisition parameter production). The set may include one or more preliminary images and/or patient information, acquisition parameters (e.g., acquisition data information, operator characteristics), etc. In one embodiment, step 303 may include receiving a designated acquisition parameter. For example, the designated parameter may be a parameter to optimize. In the following discussion, "optimizing" the parameter will be described as "minimizing" the parameter. For example, if the designated parameter is "radiation exposure" or "noise", optimizing the parameter may entail minimizing radiation exposure in acquisition or noise in an image, respectively. While other forms of optimizing parameters exist, the discussion below will focus on the exemplary embodiment where "optimizing" refers to "minimizing". In one embodiment, step 303 may include receiving a desired target minimum image quality score. In some cases, at least the set, designated acquisition parameters and/or the target minimum image quality score may be received in the form of an electronic representation (e.g., on a hard drive, cloud architecture, etc.).

In one embodiment, step 305 may include computing several patient characteristics from the preliminary images and/or patient information (e.g., received in step 301). Step 305 may include identifying parameters of patient characteristics computed in the training phase (e.g., method 200), and determining values for those same patient characteristics in the preliminary images and/or patient information received from step 301. Step 305 may further include identifying parameters of operator characteristics and determining operator characteristics associated with image acquisition and/or quality.

In one embodiment, step 307 may include receiving information specifying an acquisition device type. For example, the acquisition device type may be a type of device available in a certain setting for acquiring images. Alternately or in addition, the acquisition device type may be based on the data set (e.g., received acquisition information or acquisition device information from step 301).

In one embodiment, step 307 may then include determining a cluster related to the patient data set (e.g., received in step 301). For example, step 307 may include assigning the data set to a cluster including (training) data sets associated with an acquisition device type. The cluster may be one of several clusters including sets determined to be associated with the acquisition device type (e.g., during the training phase shown through method 200). In other words, clusters may be comprised of one or more training sets, grouped based on acquisition device type and patient information. The assignment may be based on patient characteristics (e.g., computed in step 305). The assignment may further be based on operator characteristics. In some instances, the assigned cluster may include at least one training set with an image quality score exceeding the designated minimum image quality score (e.g., from step 303). The image quality score of the training set may be based on image characteristics computed, for instance, in step 205 of method 200.

In one embodiment, step 309 may include determining a training set within the assigned cluster that has an optimal designated acquisition parameter. As previously discussed, "optimal" may mean a minimum or lowest value for a designated acquisition parameter. For example, a training set with an optimal designated acquisition parameter of noise, may have the lowest noise out of all the training sets within the assigned cluster. Determining the training set may include calculating values for the designated acquisition parameter, for each of the training sets within the assigned cluster. Furthermore, determining the training set with the optimal designated acquisition parameter may include identifying or selecting a training data set, out of the training data sets in the assigned cluster, based on the calculated values.

In one embodiment, step 311 may include the system outputting acquisition parameters associated with the training set from step 309. In some instances, the parameters may be output to an electric storage medium (e.g., hard drive, screen display, etc.). Step 313 may include acquiring a scan (e.g., cCTA) based on the output acquisition parameters.

FIG. 4 is a block diagram of an exemplary method 400 of a training phase for developing a model to predict image quality of primary imaging data from acquisition parameters, reconstructions, and various types of preliminary scans (e.g., scout scans, calcium scans, and/or contrast timing scans). The method of FIG. 4 may be performed by server systems 106, based on information, images, and data received from physicians 102 and/or third party providers 104 over electronic network 100. In one embodiment, step 401 may include a system receiving training data sets, for each of a plurality of individuals, including one or more reconstructions of medical images, one or more preliminary scans and/or patient information, acquisition parameters, acquisition device information, operator characteristics, etc. The operator characteristics may include, for instance, operator identifiers (e.g., an operator identification code), time between scans, quality of previous scans associated with the operator (or operator identification code), etc. In some cases, operators may produce images at a range of efficiency or quality. Method 400 may account for such a range in receiving operator characteristics as part of the training data sets.

In some instances, the training data sets may be in the form of electronic representations (e.g., on a hard drive, cloud architecture, etc.). In some cases, step 401 may include the system receiving multiple electronic representations, including multiple electronic representations for each training data set, multiple electronic representations for multiple training data sets, or a combination thereof.

In one embodiment, steps 403a-407 may include the system performing several computations for each of the received training data sets. For example, steps 403a-403c may include variations on a step where the system may compute several measures globally, depending on the received type of preliminary scan(s). As previously stated, the preliminary scan(s) may include a preliminary scout scan, a preliminary calcium scan, and/or a preliminary contrast timing scan.

In one embodiment involving a preliminary scout scan, step 403a may include the system computing measures of image quality and patient characteristics globally in the preliminary scout scan, where the global measures may include at least one of the following measures: image resolution, contrast level, noise level, contrast to noise ratio, motion or blurring, partial volume effect or blooming, beam hardening (e.g., as calculated by a separation of high-enhancing material and water-enhancing material by Hounsfield unity intensity on the input image), medication provided at the time of image acquisition, heart rate at the time of image acquisition, presence of anatomic abnormalities, patient anatomy, presence of implanted devices or prior surgeries, etc. In an embodiment involving a preliminary calcium scan, step 403b may include the system computing several measures of image quality globally in the preliminary calcium scan and reconstructions. The global measures may include at least one of the following metrics: image resolution, contrast level, noise level, contrast to noise ratio, motion or blurring, partial volume effect or blooming, beam hardening (e.g., as calculated by a separation of high-enhancing material and water-enhancing material by Hounsfield unity intensity on the input image), medication provided at the time of image acquisition, heart rate at the time of image acquisition, presence of anatomic abnormalities, slice thickness, misregistration or misalignment, phase of acquisition, etc. In an embodiment involving a preliminary contrast timing scan, step 403c may include the system computing several measures of image quality globally in the preliminary contrast timing scan and reconstructions. The global measures for step 403c may include at least one of the following measures: image resolution, contrast level, noise level, contrast to noise ratio, motion or blurring, partial volume effect or blooming, beam hardening (e.g., as calculated by a separation of high-enhancing material and water-enhancing material by Hounsfield unity intensity on the input image), medication provided at the time of image acquisition, heart rate at the time of image acquisition, presence of anatomic abnormalities, patient anatomy, presence of implanted devices or prior surgeries, misregistration or misalignment, phase of acquisition, etc.

Steps 405a-405c may include the system computing global and local image quality measures with respect to a primary scan. For example, step 405a may include the system computing several measures of image quality globally and in local regions of at least one reconstructed medical image defined by each coronary centerline in available reconstructions of a primary scan (e.g. a coronary computed tomography (CT) angiography scan). In some instances, the reconstructed medical image may be defined by anatomical landmarks (e.g., each centerline in all available reconstructions). In other instances, the reconstructed medical image may be defined by centerlines in a portion of the reconstructions. Coronary centerlines may be defined by running coronary artery centerline tree extraction algorithms. The global and local measures may include at least one of: image resolution, slice thickness, number of scanner slices, missing slices or missing data, length of ascending aorta in image, field of view, noise level, contrast to noise ratio, misregistration or misalignment as detected by abrupt changes in image intensity, motion or blurring as characterized by edge width or edge detection, partial volume or blooming as detected by a dramatic increase in image intensity, beam hardening (as calculated by separation of high-enhancing material and water-enhancing material by Hounsfield unit intensity on an input image), estimated sensitivity of a localized region of a coronary vessel to variation in a physiological simulation, estimated radiation dose (e.g., implied from Digital Imaging and Communications in Medicine (DICOM) header or calculated from the scan, etc. In some cases, step 405a may be executed in conjunction with an embodiment of method 400 involving a preliminary scout scan.

In one embodiment, step 405b may include the system computing several measures of image quality globally and in local regions of at least one reconstructed medical image defined by each coronary segment in available reconstructions of a primary scan. The reconstructed medical image may be defined by coronary segments in all, or a portion of the available reconstructions. Coronary segments may be identified by running coronary artery centerline tree extraction algorithms. The global and local measures may include at least one of: image resolution, slice thickness, number of scanner slices, missing slices or missing data, length of ascending aorta in image, field of view, noise level, contrast to noise ratio, misregistration or misalignment as detected by abrupt changes in image intensity, motion or blurring as characterized by edge width or edge detection, partial volume or blooming as detected by a dramatic increase in image intensity, beam hardening (as calculated by separation of high-enhancing material and water-enhancing material by Hounsfield unit intensity on an input image), estimated sensitivity of a localized region of a coronary vessel to variation in a physiological simulation, presence of implanted devices or prior surgeries, etc. In some cases, step 405b may be executed in conjunction with an embodiment of method 400 involving a calcium scoring scan. For the embodiment of method 400 including a preliminary calcium score scan, step 405c may further include computing patient characteristics (e.g., from the preliminary scans and/or patient information of step 401).

In one embodiment, step 405c may include the system computing several measures of image quality globally and in local regions of at least one reconstructed medical image defined by each coronary centerline in available reconstructions of a primary scan. The reconstructed medical image may be defined by coronary centerlines in all, or a portion of the available reconstructions. As stated previously, coronary centerlines may be identified by running coronary artery centerline tree extraction algorithms. The global and local measures may include at least one of: image resolution, slice thickness, number of scanner slices, missing slices or missing data, length of ascending aorta in image, field of view, noise level, contrast to noise ratio, misregistration or misalignment as detected by abrupt changes in image intensity, motion or blurring as characterized by edge width or edge detection, partial volume or blooming as detected by a dramatic increase in image intensity, beam hardening (as calculated by separation of high-enhancing material and water-enhancing material by Hounsfield unit intensity on an input image), estimated sensitivity of a localized region of a coronary vessel to variation in a physiological simulation, presence of implanted devices or prior surgeries, interpretability score assessing the interpretability of any given coronary segment with respect to a given local image quality, etc. In some cases, step 405c may be executed in conjunction with an embodiment of method 400 involving a contrast timing scan.

In one embodiment, step 407 may include assigning an image quality score based on the computed image quality measures from steps 405a, 405b, and/or 405c. For example, step 407 may include assigning an image quality score pertaining to each data set received in step 401. Step 407 may further include assigning image quality score(s) based on a single measure of image quality, multiple measures of image quality, particular combinations of measures for global and specified local regions, etc. In other words, step 407 may include determining image quality scores associated with a subset of the received data sets (e.g., from step 401), a subset of quality metrics, a subset of image regions or anatomies, etc.

In one embodiment, step 409 may include computing a single integrated image quality score. In one embodiment, step 409 may include computing the integrated image quality score based on the score(s) calculated in step 407. The computation may include, for example, calculating a mean, median mode, minimum value, maximum value, range, weighted mean, or any combination thereof.

In one embodiment, step 411 may include receiving image acquisition parameters, including an acquisition device type. Acquisition devices may be characterized by features including, at least, the following: CT vendor, patient characteristics (e.g., bariatric patients), scan mode (e.g., helical, axial, electrocardiography (ECG)-gated, etc.), pitch in helical mode or table feed in axial mode, rotation time, x-ray tube voltage, x-ray tube current, x-ray beam filter, x-ray beam collimation, detector configuration (e.g., 128 slices×0.7 mm), automatic exposure control, reconstruction kernel, etc. For embodiments including a preliminary scout scan and/or contrast timing scan, acquisition devices may further be characterized by an iterative reconstruction technique.

In one embodiment, step 413 may include assigning each data set to one or more clusters associated with each acquisition device type. In some embodiments, the assignments to one or more clusters may be based on features including patient characteristics and measurements or metrics computed from scout scans, calcium scoring scans, contrast timing scans for each training data set (e.g., from steps 403a, 403b, and 403c, respectively). In one embodiment, assignments in step 413 may be performed using any clustering algorithms, for example, a k-means clustering algorithm. For instance, the k-means clustering algorithm may be used to optimize assignments to clusters.

FIG. 5 is a block diagram of an exemplary method 500 of a production phase for predicting image quality of new coronary computed tomography angiograph (cCTA) images, according to an exemplary embodiment. The method of FIG. 5 may be performed by server systems 106, based on information, images, and data received from physicians 102 and/or third party providers 104 over electronic network 100.

As described above, the training phase of method 400 may include training a system to associate preliminary scout scans, calcium scoring scans, and/or contrast timing scans, device characteristics, and acquisition parameters, with local and global image quality metrics along each coronary segment. For example, method 400 may include a machine learning algorithm to train the system to recognize or learn the associations. Based on these associations, method 500 may anticipate image quality based on information given regarding, for instance, device characteristics, operator characteristics (e.g., from an operator ID), or patient information. Method 500 may further include using new acquired images as feedback to optimize or further hone the predictive capability for future scans. For example, information associated with newly acquired images may serve as an input or training data set to inform the optimization of image acquisition.

Specifically, step 501 may include receiving a data set for a particular patient, including patient information, acquisition parameters, acquisition device information, operator characteristics, and a preliminary scout image, calcium scoring image, or contrast timing image. The data set may pertain to a particular patient. In some embodiments, the acquisition device information may correspond to acquisition device information defined in a related training phase (e.g., from step 411 or 413 of method 400). In one embodiment, step 503 may include receiving a designated acquisition parameter. This parameter may be a parameter that method 500 may be used to optimize (or minimize). For example, step 503 may include receiving "estimated radiation dose" as the designated acquisition parameter.

In one embodiment, step 503 may further include receiving a designated target minimum image quality score. For example, the minimum image quality score may refer to an integrated image quality score (e.g., similar to the integrated image quality score described for step 409 of method 400). In some embodiments, the data set, designated acquisition parameter, and/or designated target minimum may be received via an electronic representation (e.g., on a hard drive, cloud architecture, etc.).

Step 505 may include computing patient characteristics and/or patient information based on the preliminary scans or images. In some embodiments, at least a portion of the patient characteristics and/or information computed in step 505 may include patient characteristics and/or patient information used in the training phase (e.g., method 400). In one embodiment, step 507 may include specifying an acquisition device type (e.g., a device type for which training data exists and/or a device type respective of the received patient data set from step 501). Step 507 may include using the patient characteristics (e.g., from step 505) and/or operator characteristics, to assign the received data set from step 501 (and associated patient) to a cluster determined in the training phase. In some embodiments, step 507 may including making the assignment such that the received data set is assigned to a cluster that includes at least one training set with an image quality score exceeding the designated minimum image quality score (e.g., from step 503).

Step 509 may include determining the training set, within the assigned cluster, with sufficient image quality scores. Such a training set may be associated with the optimal designated acquisition parameter. For this embodiment of method 500, the designated acquisition parameter is "estimated radiation dose." Therefore, step 509 may include identifying a training set associated with a minimum radiation dosage to a patient in acquiring the image(s).

In one embodiment, step 511 may include determining and/or retrieving acquisition and reconstruction parameters associated with the training set determined in step 513. For example, step 511 may include outputting the acquisition and reconstruction parameters of the determined training set in an electronic storage medium (e.g., hard drive, screen display, etc.). Furthermore, method 500 may include step 513 of acquiring an image or scan based on the acquisition parameters from step 511. For example, step 513 may include producing a primary cCTA scan based on the output acquisition parameters. In other words, the output acquisition and/or reconstruction parameters may serve as suggested or recommended parameters for future image acquisitions and/or reconstructions. Presumably, the image or scan acquired using the output acquisition parameters (e.g., from step 513) may have an image quality similar to the training data set image quality associated with the output acquisition parameters.

In some embodiments, at least information from the data set, designated target image quality score, or acquisition device type, (from steps 501, 503, or 507, respectively) may comprise a request. The request may prompt steps 511 or 513, thus causing the system to output optimized image acquisition or initiate an image acquisition based on the optimized image acquisition parameters, for example.

As previously discussed, image acquisition (e.g., from step 513) may further serve as feedback on the predicative ability of the model developed by the training phase. Images acquired using output optimized image acquisition parameters may be expected to be of a similar quality to the image quality of the training data set associated with the output image acquisition parameters, at least with respect to the designated acquisition parameter. For the image or scan of step 513 to serve as feedback, step 513 may further include determining a data set associated with the image or scan. The data set may include one or more reconstructions, one or more preliminary scans and/or patient information, and one or more acquisition parameters, consistent with the previously described training data sets.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of predicting image quality scores of images for use in operating a medical imaging scanner, the method comprising:
   determining, based on patient characteristics of one or more data sets associated with one or more data acquisition device types and an imaging procedure, a predicted image quality score for an image produced by a selected data acquisition device type for the imaging procedure; and
   determining, by a machine learning algorithm, one or more recommended device-specific image acquisition parameters associated with the predicted image quality score, the device specific-setting including: x-ray tube voltage, x-ray beam filter, detector configuration, exposure time, frames per unit time, frames per trigger, device-specific settings, scan mode, or rotation time, the machine learning algorithm having been trained to associate patient characteristics with the device-specific image acquisition parameters, and the machine learning algorithm having been trained using training data sets for each of a plurality of individuals, the sets including reconstructions of medical images, patient scout images and information, and acquisition parameters.

2. The method of claim 1, further comprising determining the one or more data acquisition device types and/or the selected acquisition device type for the imaging procedure.

3. The method of claim 1, further comprising receiving and/or storing the one or more data sets.

4. The method of claim 1, further comprising:
   determining a patient characteristic of a selected patient; and
   determining the predicted image quality score further based on the patient characteristic of the selected patient.

5. The method of claim 1, wherein the one or more recommended device-specific image acquisition parameters further includes a radiation dose.

6. The method of claim 1, further comprising:
   determining the predicted image quality score based on one or more imaging operator characteristics, one or more image characteristics, or one or more effects of imaging, wherein the one or more effects of imaging includes radiation exposure.

7. The method of claim 1, wherein the predicted image quality score is determined using machine learning.

8. The method of claim 1, further comprising:
   grouping the one or more data sets based on similarities between the patient characteristics respective to each of the one or more data sets; and
   determining the predicted image quality score based on the grouping.

9. The method of claim 1, further comprising:
   initiating or instructing production of an image based on the predicted image quality score.

10. The method of claim 9, wherein initiating or instructing production of an image includes instructing production of a computed tomography angiograph (cCTA) image.

11. The method of claim 9, including storing the image and information associated with the image as a data set included in the one or more data sets.

12. A system for predicting image quality scores of images for use in operating a medical imaging scanner, the system comprising:

a data storage device storing instructions for determining predicted image quality scores of one or more images for use in operating a medical imaging scanner; and a processor configured to execute the instructions to perform a method including:

determining, based on patient characteristics of one or more data sets associated with one or more data acquisition device types and an imaging procedure, a predicted image quality score for an image produced by a selected data acquisition device type for the imaging procedure; and determining, by a machine learning algorithm, one or more recommended device-specific image acquisition parameters associated with the predicted image quality score, the device specific-setting including: x-ray tube voltage, x-ray beam filter, detector configuration, exposure time, frames per unit time, frames per trigger, device-specific settings, scan mode, or rotation time, the machine learning algorithm having been trained to associate patient characteristics with the device-specific image acquisition parameters, and the machine learning algorithm having been trained using training data sets for each of a plurality of individuals, the sets including reconstructions of medical images, patient scout images and information, and acquisition parameters.

13. The system of claim 12, wherein the processor is further configured to perform the method comprising:

determining a patient characteristic of a selected patient; and determining the predicted image quality score further based on the patient characteristic of the selected patient.

14. The system of claim 12, wherein the system is further configured for:

determining the predicted image quality score based on one or more imaging operator characteristics, one or more image characteristics, or one or more effects of imaging, wherein the one or more effects of imaging includes radiation exposure.

15. The system of claim 12, wherein the system is further configured for:

initiating or instructing production of an image based on the predicted image quality score.

16. A non-transitory computer readable medium for use on a computer system containing computer-executable programming instructions to perform operations for predicting image quality scores of images for use in operating a medical imaging scanner; the operations comprising:

determining, based on patient characteristics of one or more data sets associated with one or more data acquisition device types and an imaging procedure, a predicted image quality score for an image produced by a selected data acquisition device type for the imaging procedure; and determining, by a machine learning algorithm, one or more recommended device-specific image acquisition parameters associated with the predicted image quality score, the device specific-setting including: x-ray tube voltage, x-ray beam filter, detector configuration, exposure time, frames per unit time, frames per trigger, device-specific settings, scan mode, or rotation time, the machine learning algorithm having been trained to associate patient characteristics with the device-specific image acquisition parameters, and the machine learning algorithm having been trained using training data sets for each of a plurality of individuals, the sets including reconstructions of medical images, patient scout images and information, and acquisition parameters.

* * * * *